(12) United States Patent
Gerson et al.

(10) Patent No.: US 11,266,861 B2
(45) Date of Patent: Mar. 8, 2022

(54) FACE MASK ASSEMBLY

(71) Applicant: Louis M. Gerson Co., Inc., Middleboro, MA (US)

(72) Inventors: Ronald L. Gerson, Middleboro, MA (US); Pierre LaPointe, Marlborough, MA (US)

(73) Assignee: Louis M. Gerson Co., Inc., Middleboro, MA (US)

( * ) Notice: Subject to any disclaimer, the term of this patent is extended or adjusted under 35 U.S.C. 154(b) by 913 days.

(21) Appl. No.: 16/004,791

(22) Filed: Jun. 11, 2018

(65) Prior Publication Data

US 2018/0289988 A1    Oct. 11, 2018

Related U.S. Application Data

(63) Continuation-in-part of application No. 14/735,631, filed on Jun. 10, 2015, now Pat. No. 9,993,668.

(51) Int. Cl.
| | | |
|---|---|---|
| *A62B 18/08* | (2006.01) | |
| *A41D 13/11* | (2006.01) | |
| *A62B 18/02* | (2006.01) | |
| *A62B 18/10* | (2006.01) | |
| *A62B 9/04* | (2006.01) | |
| *A62B 9/02* | (2006.01) | |
| *A62B 23/02* | (2006.01) | |
| *A62B 7/10* | (2006.01) | |
| *A61M 16/06* | (2006.01) | |

(52) U.S. Cl.
CPC ........ *A62B 18/084* (2013.01); *A41D 13/1161* (2013.01); *A62B 9/02* (2013.01); *A62B 9/04* (2013.01); *A62B 18/025* (2013.01); *A62B 18/10* (2013.01); *A62B 23/02* (2013.01); *A61M 16/0683* (2013.01); *A62B 7/10* (2013.01); *A62B 23/025* (2013.01)

(58) Field of Classification Search
CPC .... A62B 7/00; A62B 7/10; A62B 9/00; A62B 9/02; A62B 9/04; A62B 18/00; A62B 18/02; A62B 18/025; A62B 18/04; A62B 18/08; A62B 18/10; A62B 18/084; A62B 23/00; A62B 23/02; A61M 16/20; A61M 16/208; A61M 16/209; A61M 16/0683; A41D 13/1161

See application file for complete search history.

(56) References Cited

U.S. PATENT DOCUMENTS

| | | |
|---|---|---|
| 5,794,617 A | 8/1998 | Brunell et al. |
| 6,062,221 A | 5/2000 | Brostrom et al. |
| 6,457,473 B1 | 10/2002 | Brostrom et al. |
| 6,497,232 B2 | 12/2002 | Fecteau et al. |

(Continued)

FOREIGN PATENT DOCUMENTS

| | | |
|---|---|---|
| WO | 1995/007734 A1 | 3/1995 |
| WO | 1995007734 | 3/1995 |

(Continued)

*Primary Examiner* — Colin W Stuart
(74) *Attorney, Agent, or Firm* — Occhiuti & Rohlicek LLP

(57) ABSTRACT

A face mask includes a valve protector between a strap and an exhalation valve thereof. The valve protector's thickness defines a spacing between the strap and a strap retainer that is positioned on a mask body, disposed over the exhalation valve, and receives the strap. This spacing controls an extent of friction between the strap and the strap retainer.

11 Claims, 5 Drawing Sheets

(56) References Cited

U.S. PATENT DOCUMENTS

| | | | |
|---|---|---|---|
| 6,715,490 B2 | 4/2004 | Byram | |
| 6,732,733 B1 | 5/2004 | Brostrom et al. | |
| 7,753,051 B2 * | 7/2010 | Burrow | A62B 18/025 |
| | | | 128/207.11 |
| 8,104,472 B2 | 1/2012 | Henderson et al. | |
| 8,505,536 B2 | 8/2013 | Kielow et al. | |
| 8,839,785 B2 | 9/2014 | Castiglione et al. | |
| 9,067,086 B2 | 6/2015 | Danford | |
| 9,993,668 B2 * | 6/2018 | Gerson | A62B 18/08 |
| 2002/0078953 A1 | 6/2002 | Fecteau et al. | |
| 2002/0088466 A1 | 7/2002 | Brostrom et al. | |
| 2005/0211251 A1 | 9/2005 | Henderson et al. | |
| 2008/0156329 A1 | 7/2008 | Gerson et al. | |
| 2008/0257352 A1 | 10/2008 | Penton et al. | |
| 2010/0263673 A1 | 10/2010 | Kielow et al. | |
| 2013/0319420 A1 | 12/2013 | Danford | |
| 2014/0224256 A1 | 8/2014 | Skov et al. | |
| 2016/0361575 A1 | 12/2016 | Gerson et al. | |
| 2018/0235322 A1 * | 8/2018 | Moon | A62B 18/084 |
| 2020/0130914 A1 * | 4/2020 | Scheirlinck | B65D 77/26 |

FOREIGN PATENT DOCUMENTS

| | | |
|---|---|---|
| WO | 2016/167532 A1 | 10/2016 |
| WO | 2016/181144 A1 | 11/2016 |

* cited by examiner

FACE MASK ASSEMBLY

CROSS-REFERENCE TO RELATED APPLICATIONS

This application is a continuation-in-part of U.S. application Ser. No. 14/735,631, filed Jun. 10, 2015, the contents of which is hereby incorporated by reference in its entirety.

This invention relates to respirators and face mask assemblies.

BACKGROUND

A respirator is a device designed to protect the wearer from inhaling harmful dusts, fumes, vapors, or gases. Respirators come in a wide range of types and sizes used by the military, private industry, and the public. All respirators have some type of facepiece or mask body held to the wearer's head with straps, a cloth harness, or some other method. The mask body of the respirator covers either the entire face ("Full Face Masks") or the bottom half of the face including the nose and mouth ("Half-Masks").

Half-face mask assemblies generally include an exhalation valve that opens in response to increased pressure when the wearer exhales to allow the exhaled air to be rapidly purged from the mask interior. The inhaled (contaminated) air flows through a filter element that is generally placed over inhalation ports to purify the air that is inhaled These inhalation ports also are generally fitted with a one-way valve that closes when the user exhales in order to preserve the filters from degradation by moisture exhaled in the wearer's breath and to direct all the exhalation air through the exhalation valve or diaphragm. It is desirable that the air path between the exhalation valve and the environment be free from blockage or impediments.

SUMMARY

The invention relates to a face mask configured to be worn on a wearer's head and to cover the wearer's nose and mouth. In a general aspect of the invention, the face mask comprises a mask body having a plurality of apertures; an exhalation valve positioned within one of the plurality of apertures of the mask body; a harness assembly configured to extend about the wearer's head wherein the harness assembly; a first strap attached to the harness assembly, a strap retainer positioned on the mask body and disposed over the exhalation valve, the strap retainer configured to receive the first strap; and a valve protector. The first strap has a front surface and a rear surface, opposite the front surface, the front surface and the rear surface defining a second thickness therebetween. The valve protector is positioned between the first strap and the exhalation valve, the valve protector having a first surface configured to engage the exhalation valve and a second surface, opposite the first surface, the first surface and the second surface defining a first thickness therebetween such that a spacing between the first strap and the strap retainer is configured to control the friction between the first strap and the front surface of the strap retainer.

Embodiments of this aspect of the invention may include one or more of the following features.

The spacing between the first strap and the exhalation valve is substantially the same as the second thickness of the first strap. One of the front surface and the rear surface of the first strap engages one of the first surface and the second surface of the exhalation valve. The front surface of the first strap engages the first surface of the exhalation valve and the rear surface of the first strap engages the second surface of the exhalation valve.

The face mask further includes a second strap and the strap retainer is configured to guide the first strap and the second strap in a crossed configuration. The first strap and second strap cross at the valve protector and the first strap and the second strap contact the valve protector. The harness assembly is adapted for retaining the mask body at a first position covering a wearer's nose and mouth, and at a second position dropped down from a wearer's face without removing the harness assembly from a wearer's head. The spacing between the outer surface of the valve protector and the inner surface of the strap retainer is substantially that of the thickness of the crossed straps. The face mask of second surface of the valve protector includes at least one region underlying the first strap, the at least one region defining a region of friction. For example, the second surface of the valve protector may include protuberances in the at least one region of friction. The valve protector may be ring-shaped.

In another embodiment, the valve protector includes an upper semicircular region and a lower semicircular region, the upper semicircular region of the valve protector having a dome shape.

Among other advantages, a face mask having the configuration described above allows for the resistance between the right and left straps to be increased as they pass through corresponding slots of strap retainer 40. Increasing the resistance between the straps and slots will also allow the face mask to be positioned in a stationary manner over the nose and mouth of the wearer, so that the wearer's hands are free to attach and adjust the tension of the head harness around the neck to enable a tight fit of the mask to face. If the face mask does not have sufficient tension to the head harness straps, then the mask will slide down the face of the wearer, making it difficult to obtain the correct tension and fit of the mask to the face.

Other features and advantages of the invention are apparent from the following description, and from the claims.

DESCRIPTION

Figure 1:
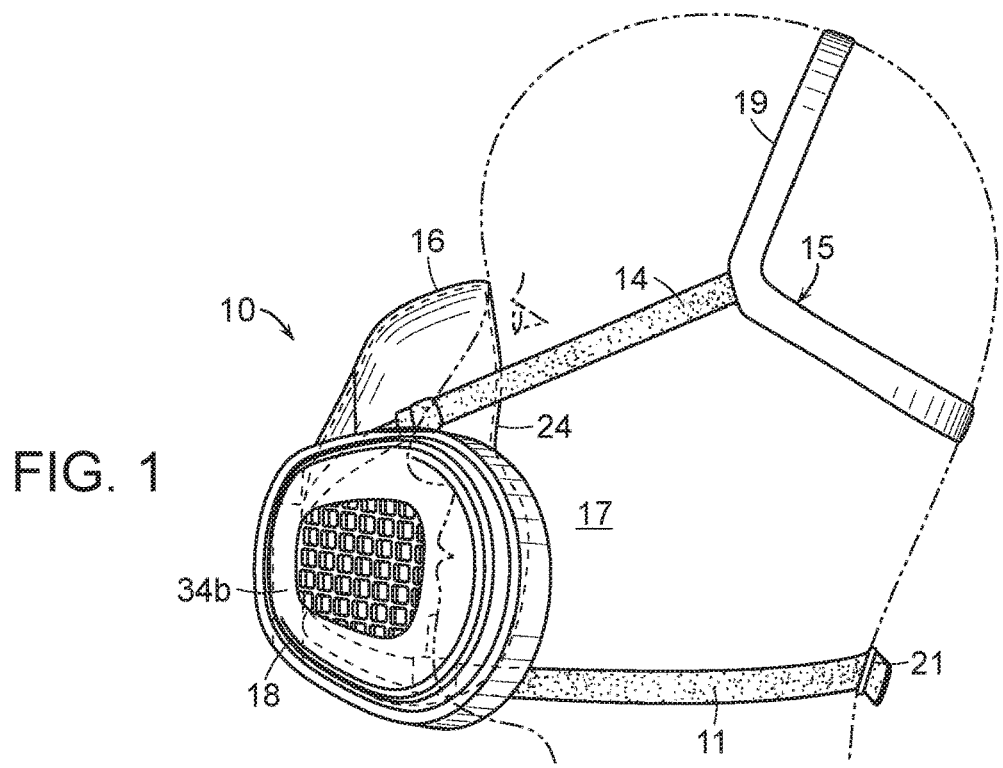
FIG. 1 is a side view of a face mask assembly worn on a wearer's head.

Referring to FIG. 1, a representative face mask 10 is shown held against a wearer's face 17 with a harness assembly 15 having a right adjustable strap 12, a left adjustable strap 14 and a lower adjustable strap 11 so that a face piece 16 having a face shaped flange rim 24 covers and seals the user's nose and mouth. Right strap 12 and left strap 14 are attached to a head cradle 19 while lower strap 11 is attached to a release buckle 21. When the mask is worn, the user inhales filtered ambient air through preferably removably mounted conventional filters 18, which are positioned on the sides of the face mask, and exhales air through a conventional flapper and exhalation valve 34 (FIG. 2) at the front of the mask. To comfortably conform to the user's face, face piece 16 is preferably made at least in part from a soft, deformable, preferably resilient or elastomeric material, and can be made in various sizes to accommodate different users.

As will be discussed in greater detail below, harness assembly 15 with its right and left adjustable straps 12, 14, is configured to attach to face mask 10, through a strap retainer 40 (discussed in greater detail below), such that the face mask can be easily adjusted and to conform to different wearer's faces. The configuration also allows the face mask 10 to be moved between multiple positions without removing the harness assembly. For example, face mask 10 can be worn at a first position with the face piece 16 and face shaped rim 24 covering and sealing the user's nose and mouth. In a second position, face mask 10 can be dropped from the wearer's face to a second position without moving the harness assembly from the head of the wearer. If the wearer is using, for example, a protective hard-hat, this is a particularly desirable feature. In this second position, face mask 10 hangs near the wearer's body in a dropped down position. This is advantageous in situations where the wearer needs to access his or her mouth (e.g., to speak) or otherwise needs to remove the face mask without having to remove the face mask altogether and then reposition the face mask over the wearer's mouth and nose when work recommences. Also, in the second position, face mask 10 hangs off of the wearer's body so that does not have to be placed on the ground or stored elsewhere.

Face piece 16 is in the form of a deformable resilient face-shaped member having an outer wall that supports the exhalation valve housing and inhalation valves as well as an encircling rim formed by the face piece that is shaped to contact and conform to the wearer's face thereby forming a seal against the face when the face mask is positioned on the wearer. The encircling rim has an edge defined by outer face piece walls extending away from the rim. The face piece 16 defines an interior portion of the face piece that forms a breathing chamber, and an encircling bent back rim portion 23 extending from the encircling rim and toward the interior of the face piece.

Face piece 16 is made from a molded polymeric elastomeric material as by compression, injection or vacuum molding of materials, such as polyvinylidene chloride, natural rubber, synthetic rubbers such as silicone, neoprene, PVC, or urethane.

Figure 2:
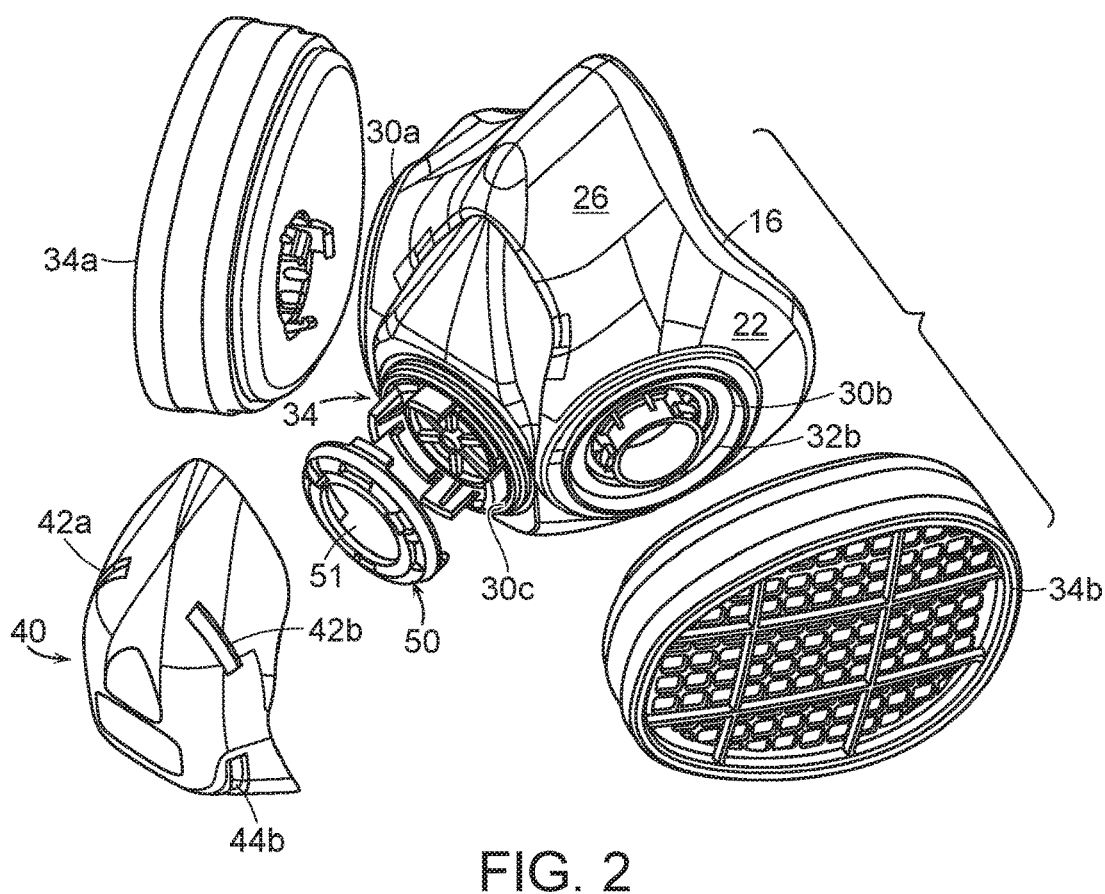
FIG. 2 is a front, exploded perspective view of the face mask assembly of FIG. 1 (without harness assembly).
Figure 3:
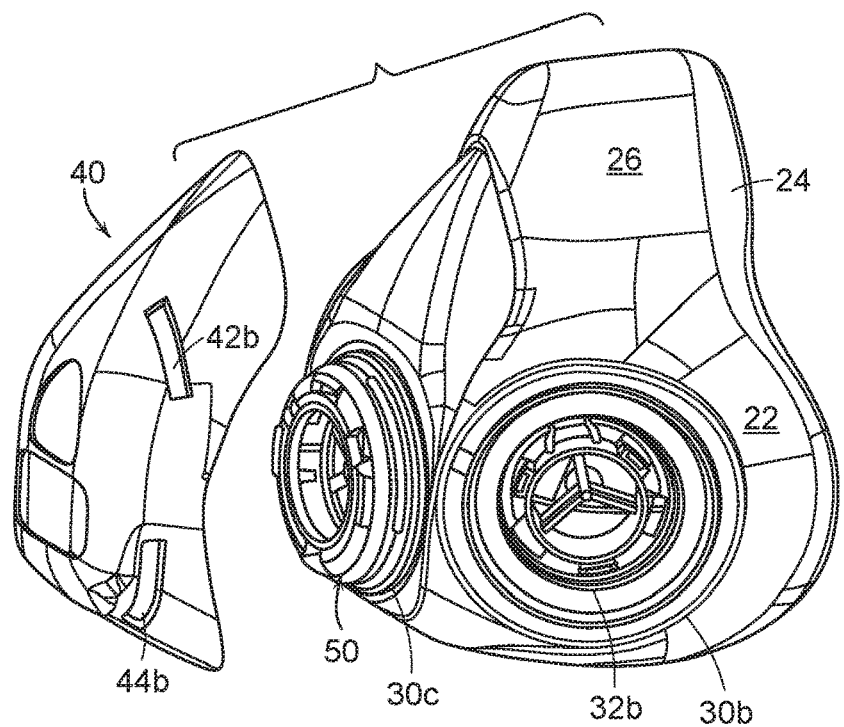
FIG. 3 is a partially exploded perspective view of the face mask assembly of FIG. 1.

Referring to FIGS. 2 and 3, face piece 16 has a preferred thickness between about 0.015 to 0.125 inches and is preferably at least about 0.032 inches. The thickness can vary within a single face piece from about 0.032 at the inner edges of the bent back portion 26 to provide greater flexibility, to about 0.125 at the outer sides 22 where greater support is needed. At such thickness and selected durometer, the material of the bent back portion 26 has sufficient durability, softness, and deformability to comfortably form a good seal with the face of a user, while not being too flimsy.

Face piece 16 has a pair of side apertures 30a, 30b, one on each side of face piece 16 with a third aperture 30c positioned between the side apertures. Apertures 30a, 30b are sized and shaped to receive corresponding inhalation valves 32a, 32b which are configured to receive removable filter cartridges 34a, 34b for filtering particulates and/or gases. As can be seen in FIG. 2, filter cartridges 34a, 34b are of the type that uses a bayonet mount arrangement for attaching to face piece 16. Third aperture 30c is sized and shaped to receive an exhalation valve 34 such that when face mask 10 is placed on the wearer's face, exhalation valve is positioned over the wearer's mouth. Exhalation valve 34 is of the type having a flexible diaphragm.

Face mask 10 includes a strap retainer 40 that is adapted to attach to face piece 16 and over exhalation valve 34. Strap retainer 40 is in the form of a concave shell for accommodating the exhalation valve, as well as straps 12, 14 and attachment elements 48, configured to be received by corresponding slots 56 in the valve protector 50. When strap retainer 40 is positioned on face piece 16 the two components conform to provide a unitary, smooth, and contoured face mask 10. Strap retainer 40 is configured to receive and support straps 12, 14 at four points of engagement. The four engagement points are in the form of a pair of upper slots 42a, 42b and a pair of lower slots 44a, 44b. Each of the upper slots 42a, 42b and lower slots 44a, 44b is rectangular in shape and suitably sized to allow right strap 12 and left strap 14 to pass through without resistance. Strap retainer 40 includes, at its lower end, an opening 46 through which air from exhalation valve 34 is expelled. Opening 46 is positioned on strap retainer 40 such that, when face mask 10 is in use, the opening is directed in a downward direction. Positioned in this way, the diaphragm in the exhalation valve is covered and the chance for debris, fragments, paint overspray, or other particulates entering the mask and contaminating the exhalation diaphragm is minimized.

Figure 4:
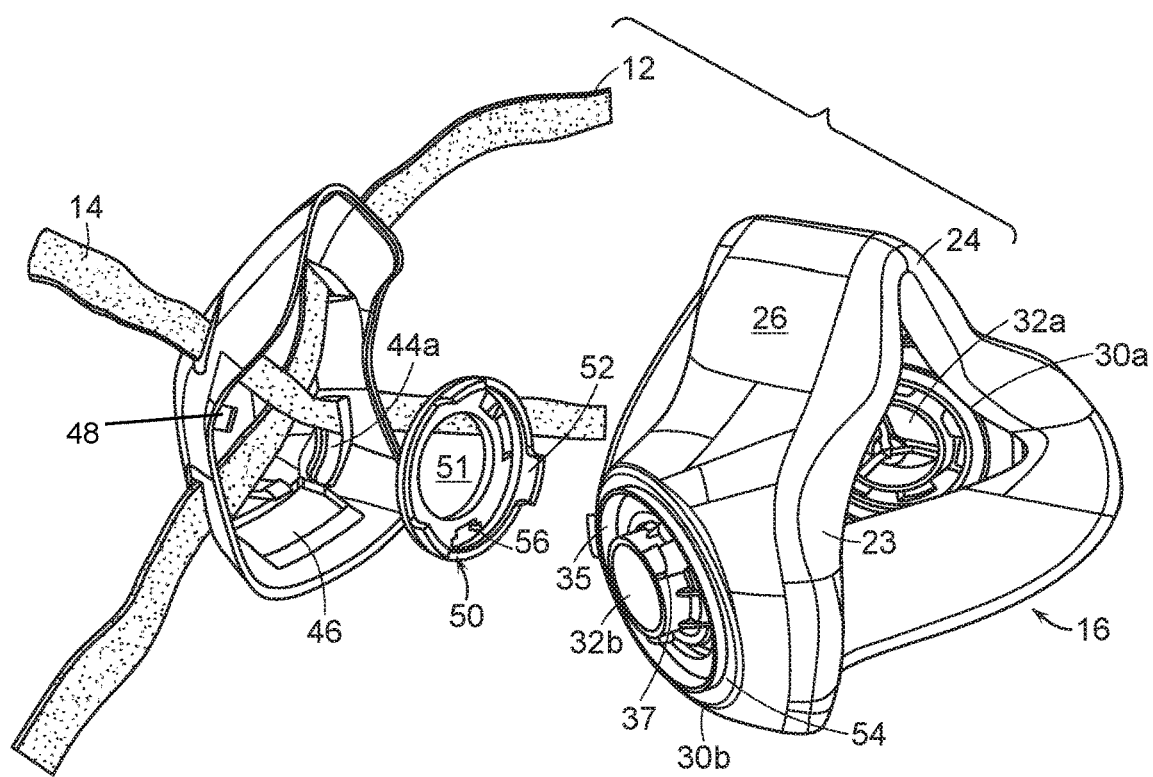
FIG. 4 is a rear, exploded perspective view of the face mask assembly of FIG. 1 showing the configuration of straps and strap retainer.

Referring to FIG. 4, right strap 12 and left strap 14 extend through upper slots 42a, 42b and lower slots 44a, 44b in crosswise fashion. Right strap 12 and left strap 14 extend in crosswise fashion because generally there is not sufficient space between opening 30c for supporting the exhalation valve 34 and cartridges 34a and 34b when they are positioned on inhalation valve apertures 30a, 30b for them to run vertically, rather than crosswise, through the slots. Right strap 12 extends through upper slot 42a and lower slot 44b while left strap 14 extends through upper slot 42b and lower slot 44a. With this arrangement, there is a risk that right strap 12 and left strap 14 can contact and impede airflow through a diaphragm flapper of exhalation valve 34, particularly at the intersection of the straps between the exhalation valve and the inner surface of strap retainer 40.

Figure 5:
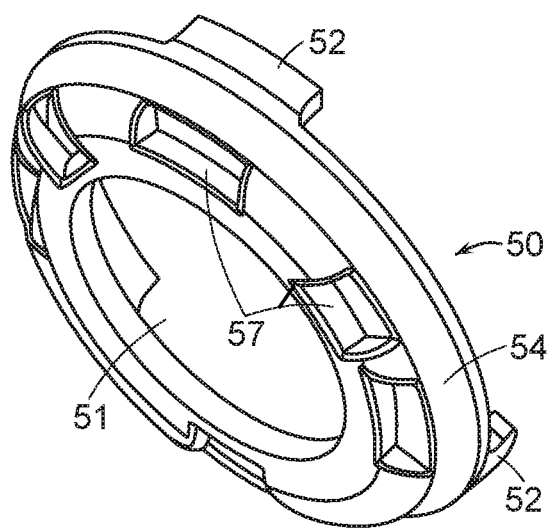
FIG. 5 is a front perspective view of the valve protector of FIG. 1.

Referring to FIGS. 2, 4 and 5, to ensure adequate airflow and to minimize the possibility that right strap 12 and left strap 14 block the air path to exhalation valve 34, face mask 10 includes a valve protector 50. Valve protector 50 is dome-shaped such that the straps will be prevented from contacting and spaced from the front surface of exhalation valve 34 and is in the form of a ring (ring-shaped) that defines an aperture 51 over the exhalation valve. Valve protector 50 includes a set of radially-spaced tabs 52 positioned on a peripheral wall 54, each tab 52 being sized and configured to engage an outer lip of exhalation valve 34. Exhalation valve housing 35, in turn, includes a set of radially-spaced tabs 37 that are sized and configured to be received within appropriately sized and shaped radial slots 57 of valve protector 50.

In the embodiment shown in FIG. 5, the peripheral wall 54 of the valve protector 50 is sized and shaped to allow the right strap 12 and the left strap 14 to move with limited resistance through corresponding upper slots 42a, 42b and lower slots 44a, 44b of strap retainer 40.

However, in certain applications, the filter mask, when assembled with removable filter cartridges 34a, 34b may weigh up to 600 grams/pair. In such applications, the weight of the filter mask, together with the filter canisters, when released from the wearer's face, will drop to the bottom of the strap and hang well below the wearer's face.

In such situations, it may be desirable to increase the resistance between the right strap 12 and the left strap 14 as they pass through corresponding slots 42a, 42b and lower slots 44a, 44b of strap retainer 40. Increasing the resistance between the straps and slots will also allow the face mask to be positioned in a stationary manner over the nose and mouth of the wearer, so that the wearer's hands are free to attach and adjust the tension of the head harness around the neck to enable a tight fit of the mask to face. If the face mask 10 does not have sufficient tension to the head harness straps 12 and 14, then the mask will slide down the face of the wearer, making it difficult to obtain the correct tension and fit of the mask to the face.

Therefore, in such situations, other embodiments of the face mask 10 may include a valve protector 50 that is sized and shaped to increase the resistance of the right strap 12 and the left strap 14 through corresponding upper slots 42a, 42b and lower slots 44a, 44b of strap retainer 40. For example, valve protector 50 may have an increased thickness such that the space between the outer surface of valve protector 50 and the inner surface of strap retainer 40 is substantially that of the thickness of straps 11, 12. Reducing the spacing between the outer surface of valve protector and the inner surface of strap retainer 40 provides increased frictional contact.

More particularly, the right strap 12 and the left strap 14 both have a front surface and an opposite rear surface, which define therebetween, the thicknesses of the straps. In these embodiments in which increased frictional contact between the valve protector and the strap retainer is desired, the spacing between the outer surface of valve protector and the inner surface of strap retainer 40 as well as the thicknesses of the right strap 12 and the left strap 14 are configured such that the both the front surfaces and rear surfaces of the straps 12, 14 engage the inner surface of the strap retainer and the outer surface of the valve protector, respectively. It is the engagement of the front and rear surfaces which cause the frictional contact. Furthermore, the spacing and the extent to which the surfaces engage will determine the extent of friction between those surfaces.

Figure 6:
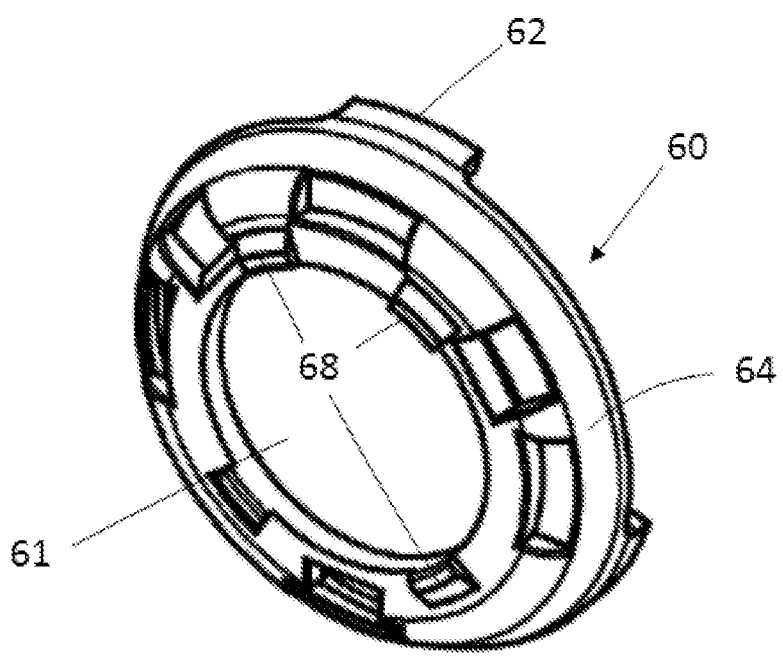
FIG. 6 is a front perspective view of an alternative embodiment of a valve protector.

In another embodiment, as shown in FIG. 6, a valve protector 60 includes four protrusions 68 on the outer surface of the valve protector 60 that are positioned to make frictional contact with the crisscrossed right strap 12 and left strap 14. In this embodiment, rather than increasing the overall thickness of the valve protector 60, protrusions 68 provide specific areas where frictional contact is provided to the straps 12, 14. It should be appreciated that fewer than four protrusions (e.g., one for each strap) may be all that may be required to provide the necessary resistance. The valve protector 60 is in other ways configured as previously described for the valve protector 50 of FIGS. 1-5, with an aperture 61 over the exhalation valve 34 and radially-spaced tabs 62 positioned on a peripheral wall 64, each tab 52 being sized and configured to engage an outer lip of exhalation valve 34.

Figure 7:
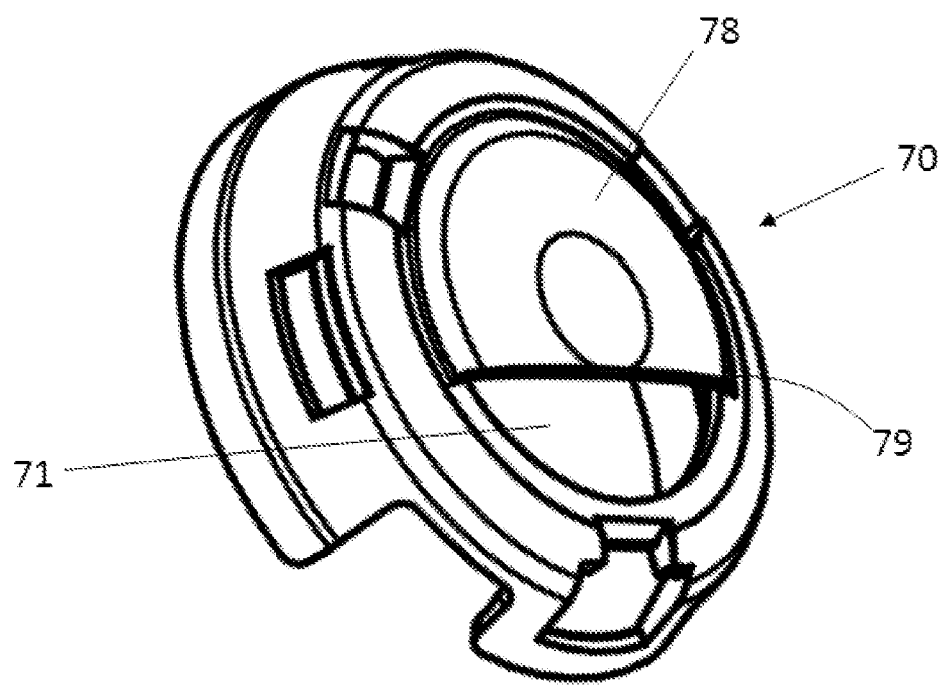
FIG. 7 is a front perspective view of another alternative embodiment of a valve protector configured with a semicircular dome to frictionally engage straps, to protect the exhalation valve from contamination and to direct exhaust air downwards.

In yet another embodiment, as shown in FIG. 7, the circular center of the valve protector 70 has an upper semicircular region and a lower semicircular region. The upper semicircular region of the valve protector 70 is covered by a semicircular dome 78. The semicircular dome 78 is delimited by a chord 79 from a semicircular opening 71 below the chord 79. The semicircular dome 79 has a convex surface that provides frictional contact to the straps 12, 14. The degree of frictional force exerted by the semicircular dome 79 can be adjusted by adjusting the height of the dome. As an additional advantage provided by this embodiment, the dome protects the exhalation valve 34 from contamination from any particulates from the work environment that may have attached onto the straps and that could be dislodged as the straps move between the strap retainer and the valve protector. Finally, the lower semicircular opening 71 is positioned to direct air downward towards the opening 46 through which air from exhalation valve 34 is expelled. Directing air downward in this manner reduces fogging of eyewear and protective shields that may be used in combination with the respirator.

It is to be understood that the foregoing description is intended to illustrate and not to limit the scope of the invention, which is defined by the scope of the appended claims. For example, although the harness assembly is described as having a pair of separate straps, in certain embodiments, a single strap can be used with the strap retainer. Other embodiments are within the scope of the following claims.

What is claimed is:

1. A face mask configured to be worn on a wearer's head and to cover the wearer's nose and mouth, the face mask comprising:
    a mask body having a plurality of apertures;
    an exhalation valve positioned within one of the apertures of the mask body;
    a harness assembly configured to extend about the wearer's head;
    a first strap attached to the harness assembly, the first strap having a front surface and a rear surface opposite the front surface, the front surface and the rear surface defining a strap thickness therebetween;
    a strap retainer positioned on the mask body and disposed over the exhalation valve, the strap retainer configured to receive the first strap; and
    a valve protector positioned between the first strap and the exhalation valve, the valve protector having a first surface configured to engage the exhalation valve and a second surface that is opposite the first surface, the first surface and the second surface defining a valve-protector thickness therebetween,
    wherein the valve-protector thickness defines a spacing between the first strap and the strap retainer, and wherein the spacing controls an extent of friction between the front surface of the first strap and the strap retainer.

2. The face mask of claim 1, wherein the spacing between the first strap and the strap retainer is substantially the same as the strap thickness of the first strap.

3. The face mask of claim 1, wherein the first strap engages second surface of the valve protector.

4. The face mask of claim 1, wherein the first strap engages both the valve protector and the strap retainer.

5. The face mask of claim 1, further comprising a second strap, wherein the strap retainer is configured to guide the first strap and the second strap in a crossed configuration, the first strap and second strap crossing at the valve protector, wherein the first strap and the second strap contact the valve protector.

6. The face mask of claim 1, wherein the harness assembly is adapted for retaining the mask body at a first position, in which the mask body covers a wearer's nose and mouth and at a second position, in which the mask body is dropped down from a wearer's face without the harness assembly having been removed from a wearer's head.

7. The face mask of claim 1, further comprising a second strap, wherein the strap retainer guides the first and second straps so that they cross over each other, wherein a combined thicknesses of the straps is substantially that of a space between the valve protector and the strap retainer.

8. The face mask of claim 1, wherein the valve protector is ring-shaped.

9. The face mask of claim 1, wherein the second surface of the valve protector includes at least one region underlying the first strap, the at least one region defining a region of friction.

10. The face mask of claim 9, wherein the second surface of the valve protector includes protuberances in the region of friction.

11. The face mask of claim 1, wherein the valve protector includes an upper semicircular region and a lower semicircular region, the upper semicircular region of the valve protector having a dome shape.

\* \* \* \* \*